US012019060B2

(12) United States Patent
Chen et al.

(10) Patent No.: US 12,019,060 B2
(45) Date of Patent: Jun. 25, 2024

(54) USSING CHAMBER DEVICES, SYSTEMS, AND METHODS OF USE THEREOF

(71) Applicant: Colorado State University Research Foundation, Fort Collins, CO (US)

(72) Inventors: Thomas W. Chen, Fort Collins, CO (US); Caleb R. Begly, Colorado Springs, CO (US); Michael Siegel, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 327 days.

(21) Appl. No.: 17/225,809

(22) Filed: Apr. 8, 2021

(65) Prior Publication Data
US 2021/0318286 A1  Oct. 14, 2021

Related U.S. Application Data

(60) Provisional application No. 63/006,912, filed on Apr. 8, 2020.

(51) Int. Cl.
*G01N 33/483*  (2006.01)
*B01L 3/00*  (2006.01)
*G01N 27/04*  (2006.01)

(52) U.S. Cl.
CPC .... *G01N 33/4833* (2013.01); *B01L 3/502715* (2013.01); *G01N 27/041* (2013.01);
(Continued)

(58) Field of Classification Search
CPC .............. G01N 33/4833; G01N 27/041; B01L 3/502715; B01L 2300/0627; B01L 2300/0867
See application file for complete search history.

(56) References Cited

U.S. PATENT DOCUMENTS 4,862,092 A * 8/1989 Juncosa ............. G01N 33/4833
324/692
5,738,826 A * 4/1998 Lloyd ................ G01N 33/4833
422/547
(Continued)

FOREIGN PATENT DOCUMENTS

CN         109576155 A  *  4/2019  ............ C12M 23/16

OTHER PUBLICATIONS

Translation of CN109576155A, Sun, Chang-kai, Apr. 5, 2019 (Year: 2019).*

(Continued)

*Primary Examiner* — Samuel P Siefke
*Assistant Examiner* — Henry H Nguyen
(74) *Attorney, Agent, or Firm* — Meunier Carlin & Curfman LLC

(57) ABSTRACT

An Ussing chamber assembly for assessing a tissue sample and for receiving a first fluid and a second fluid during such assessment is disclosed. The Ussing chamber assembly includes an Ussing chamber configured to be separated by the tissue sample into a first chamber portion and a second chamber portion. The assembly includes a first channel in fluidic communication with the first chamber portion, a second channel in fluidic communication with the second chamber portion, and at least three electrical conductors in fluidic communication with the first chamber portion.

20 Claims, 7 Drawing Sheets

(52) U.S. Cl.
CPC ............... *B01L 2300/0627* (2013.01); *B01L 2300/0867* (2013.01)

(56) References Cited

U.S. PATENT DOCUMENTS

| | | | | |
|---|---|---|---|---|
| 2015/0004077 | A1* | 1/2015 | Wikswo | C12M 29/10 422/502 |
| 2016/0175840 | A1* | 6/2016 | Ingber | B01L 3/56 29/428 |
| 2016/0332119 | A1* | 11/2016 | Fissell | A61B 5/14532 |

OTHER PUBLICATIONS

Ramadan et al., "In vitro micro-physiological immune-competent model of the human skin", 2016, Lab Chip, 16, 1899 (Year: 2016).*
Maoz et al., "Organs-on-Chips with combined multi-electrode array and transepithelial electrical resistance measurement capabilities", 2017, Lab on a chip, 17, 2294-2302 (Year: 2017).*

* cited by examiner

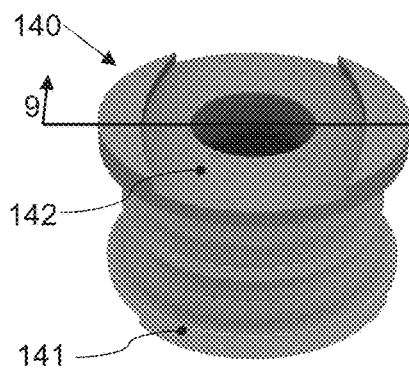
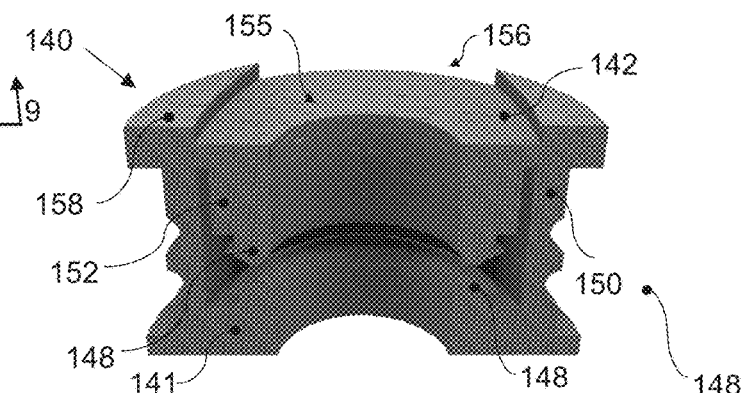
FIG. 8    FIG. 9
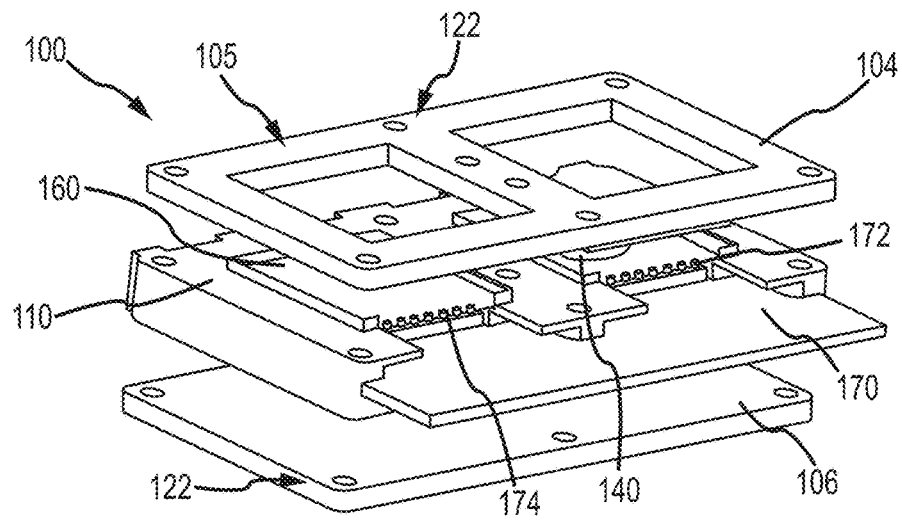
FIG. 10
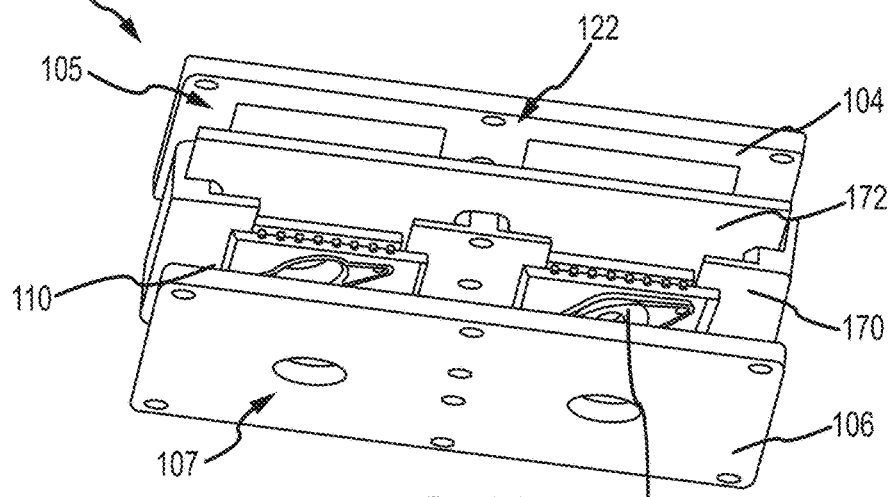
FIG. 11

USSING CHAMBER DEVICES, SYSTEMS, AND METHODS OF USE THEREOF

CROSS REFERENCE TO RELATED APPLICATION

This application claims priority from U.S. provisional patent application No. 63/006,912, titled "Ussing Chamber Design," filed on Apr. 8, 2020, the entirety of which is incorporated by reference herein.

FIELD OF THE INVENTION

This application relates to devices, systems, and methods for studying biological tissue. In particular, this application relates to Ussing chamber devices, systems, and methods of use thereof for studying biological tissue.

BACKGROUND OF THE INVENTION

Some current Ussing chambers suspend tissue with glassware and supply nutrients to each side of the tissue with separate glass tubes. Further, these Ussing chambers typically use benchtop instrumentation for measuring parameters one at a time. Such Ussing chambers tend to be bulky and limited in the information they can derive during a particular test setup. Furthermore, these Ussing chambers do not lend themselves to scalability of analyzing multiple biological tissues at the same time with measurements of multiple parameters. Therefore, their commercial usefulness may be limited. Thus, a need exists to provide a more compact Ussing chamber having integrated instrumentation and supporting fluidic/microfluidic system for measuring multiple parameters on multiple biological tissues simultaneously during a test setup.

SUMMARY OF THE INVENTION

In a first exemplary embodiment of the present invention, an Ussing chamber assembly for assessing a tissue sample and for receiving a first fluid and a second fluid during such assessment is disclosed. The assembly may include an Ussing chamber configured to be separated by the tissue sample into a first chamber portion and a second chamber portion, a first channel in fluidic communication with the first chamber portion, a second channel in fluidic communication with the second chamber portion, and at least three electrical conductors in fluidic communication with the first chamber portion.

In some versions of the first embodiment, the assembly may further comprise a measurement circuit configured to measure a Trans-Epithelial Electrical Resistance and at least one of pH, oxygen level, glucose level, and lactose level in the first chamber portion. Further, the measurement circuit may be configured to measure at least one of pH, oxygen level, glucose level, and lactose level in the second chamber portion. The measurement circuit may be configured to measure at least two of pH, oxygen level, glucose level, and lactose level in the first chamber portion. The measurement circuit may also be configured to measure at least three of pH, oxygen level, glucose level, and lactose level in the first chamber portion. Additionally, microscopy may be configured to be performed separately on both the first and second chamber portions while the first fluid is flowing through the first channel and the second fluid is flowing through the second channel. Moreover, the Ussing chamber may be configured to be rotated 90 degrees in any of three different orthogonal directions during a measurement and while the first fluid is flowing in the first channel and while the second fluid is flowing in the second channel.

In a second exemplary embodiment of the present invention, a measurement device configured for measuring one or more properties of two separate sides of a tissue sample and for receiving a first fluid and second fluid during such measurement is disclosed. The device may include a housing including a first chamber portion and a second chamber portion, the first and second chamber portion configured to be separated by a tissue sample, a first channel within the housing in fluidic communication with the first chamber portion, a second channel within the housing in fluidic communication with the second chamber portion, and at least two electrical conductors in the housing configured to measure a property of the tissue sample. The housing may be configured to be rotated 90 degrees in any of three different orthogonal directions during a measurement and while the first fluid is flowing in the first channel and while the second fluid is flowing in the second channel.

In some versions of the second exemplary embodiment, microscopy may be configured to be performed separately on both the first and second chamber portions while fluid is flowing through the first channel and second fluid is flowing through the second channel. The device may further include a measurement circuit configured to measure a Trans-Epithelial Electrical Resistance and at least one of pH, oxygen level, glucose level, and lactose level in the first chamber portion. Also, the measurement circuit may be configured to measure at least two of pH, oxygen level, glucose level, and lactose level in the first chamber portion. The measurement circuit may be configured to measure at least three of pH, oxygen level, glucose level, and lactose level in the first chamber portion. In addition, the measurement circuit may be configured to measure at least one of pH, oxygen level, glucose level, and lactose level in the second chamber portion. Further, a largest dimension of the housing in a first direction may be less than 5 cm.

In a third exemplary embodiment of the present invention, a measurement device configured for measuring one or more properties a tissue sample and receiving a first fluid from a first removable fluid source and a second fluid from a second removable fluid source during such measurement is disclosed. The device may include an Ussing chamber having a first chamber portion and a second chamber portion separated by a tissue sample, the first chamber portion having a first integrated fluid port configured to be connected to the first removable fluid source, and the second chamber portion having a second integrated fluid port configured to be connected to the second removable fluid source. A largest dimension of the Ussing chamber in a first direction may be less than 5 cm.

In some versions of the third exemplary embodiment, a largest dimension of the Ussing chamber in the first direction may be less than 4 cm. A largest dimension of the Ussing chamber in a second direction orthogonal to the first direction may be less than 4 cm. Also, a largest dimension of the Ussing chamber in a third direction orthogonal to the first and second directions may be less than 3 cm. Microscopy may be configured to be performed separately on both the first and second chamber portions while the first fluid is flowing through the first channel and second fluid is flowing through the second channel. Further, the Ussing chamber may be configured to be rotated 90 degrees in three different orthogonal directions during a measurement and while the first fluid is flowing in the first channel and while the second fluid is flowing in the second channel.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 8 is a top, front perspective view of an insert subassembly including the upper and lower inserts from FIGS. 4 and 6.

FIG. 9 is a top, front perspective sectional view of the insert subassembly from FIG. 8 taken along the section line 9-9.

FIG. 10 is a top, front, right-side perspective view of a partially assembled Ussing chamber including the partially assembled Ussing chamber from FIG. 1.

FIG. 11 is a bottom, rear, left-side perspective view of the partially assembled Ussing chamber from FIG. 10.

DETAILED DESCRIPTION

Reference will now be made in detail to the exemplary embodiments, which are illustrated in the accompanying drawings. Wherever possible, the same reference numbers will be used throughout the drawings to refer to the same or like parts.

Figure 1:
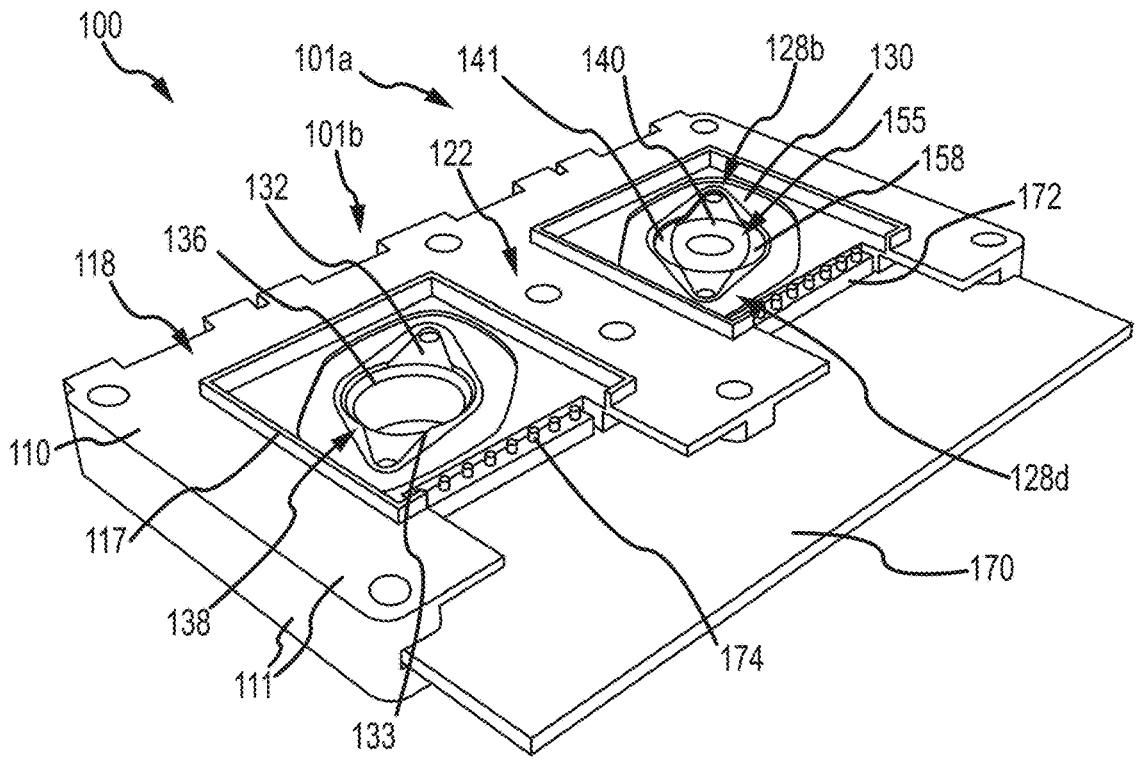
FIG. 1 is a top, front, left-side perspective view of a partially assembled Ussing chamber according to an exemplary embodiment of the present disclosure.
Figure 2:
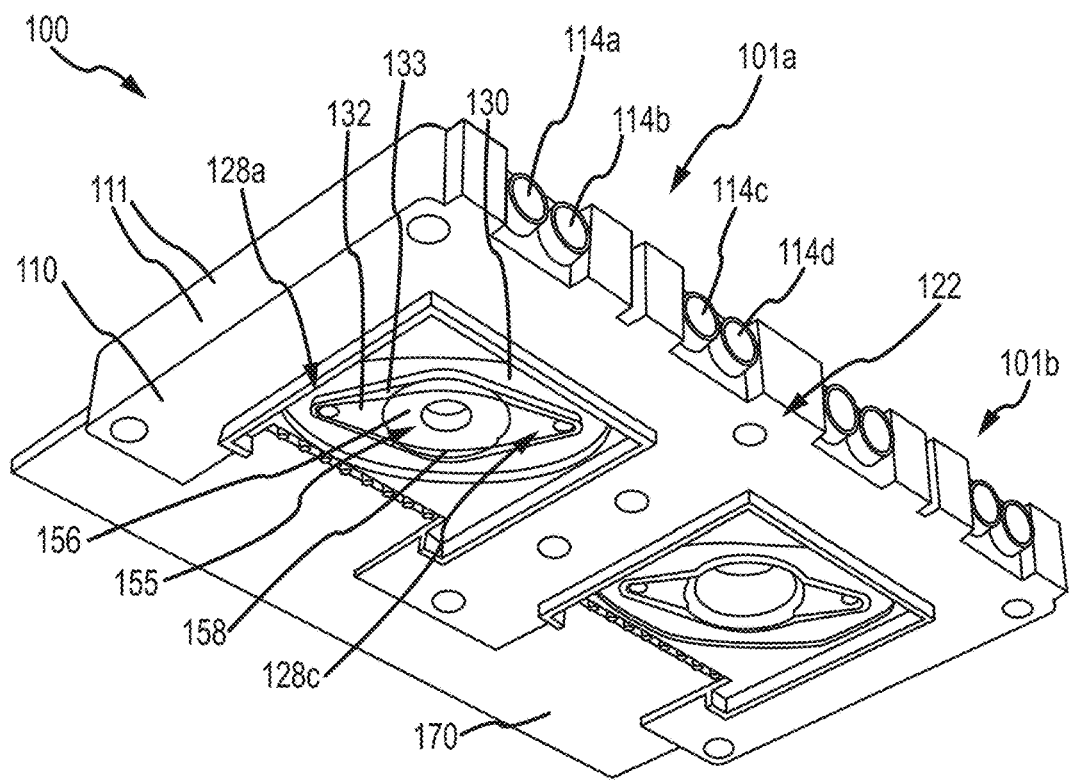
FIG. 2 is a bottom, rear, right-side perspective view of the partially assembled Ussing chamber of FIG. 1.

Described herein are Ussing chamber devices, systems, and methods of use thereof. FIGS. 1, 2, 10, and 11 depict an exemplary embodiment of an Ussing chamber assembly 100 for measuring properties of biological tissue membranes, such as the epithelium, which lines the outer or inner surfaces of organs and blood vessels throughout the body. In particular, FIGS. 1 and 2 show a partially assembled Ussing chamber assembly 100 including a housing 110 which is configured to house an insert subassembly 140 for holding a tissue sample (not shown) to be analyzed, and a breakout board 170 for connecting electrodes to a circuit board 180. FIGS. 10 and 11 further depict the partially assembled Ussing chamber assembly 100 with a glass cover 160 having integrated electrodes 162 (shown in FIG. 12) for measuring one or more parameters and upper and lower clamps 104, 106 for applying a compressive force to ultimately be transmitted to the insert to hold the tissue sample in compression. Each of these components are discussed in more detail below.

Returning to FIGS. 1 and 2, the housing 110 is discussed in more detail. The housing 110 may be comprised of two housing halves 111 each having an outer side surface 112 and an inner side surface 113 (shown in FIG. 3). The housing halves 111 may be identical to each other for efficient manufacturing and assembly, such that the inner side surface 113 of a first housing half 111 is assembled to face and mate against the inner side surface 113 of a second housing half 111. Further, the housing halves 111 may be comprised of a polymeric material, such as PTFE or COC, lending itself to a molding process. However, in other embodiments not shown, the housing halves 111 may have distinct upper and lower halves or the housing 110 may be a single component. The housing 110 may be configured to partially form two Ussing chambers 101a, 101b, i.e., two separate chambers configured to independently test two different tissue samples simultaneously. However, in other embodiments, the housing 110 may be configured to partially form a single Ussing chamber or may be configured to partially form any number of Ussing chambers, such as, for example, 4, 6, 8, 10, 12, 16, 20, 24, 32, 48, 64, or 96 Ussing chambers.

FIG. 1 shows a top, front, left-side perspective view of the Ussing chamber assembly 100 with only one of the insert subassemblies 140 assembled in a first Ussing chamber 101a to more easily identify that insert subassembly 140 and associated features of the housing 110 on the opposite side of the Ussing chamber assembly 100 as shown in a bottom, rear, right-side perspective view of the Ussing chamber assembly 100 in FIG. 2. In addition to holding the insert subassembly 140 and glass cover 160, the housing 110 is also configured to route fluids to the insert subassembly 140. In particular, the housing 110 may define a plurality of fluidic/microfluidic channels to deliver and remove fluids to and from both sides of the insert subassembly 140, such as channels that have a diameter of 2.5 mm or less, preferably 2.2 mm or less.

Exemplary pathways of the microfluidic channels for delivering and removing fluid to and from the particular insert subassembly 140 in the first Ussing chamber 101a shown in FIGS. 1 and 2 will be described next. It should be noted that the same pathways are repeated for each Ussing chamber, i.e., the second Ussing chamber 101b using the same part numbers. For example, as shown in FIG. 2, a lower inlet port 114a is the starting point of a fluid pathway through the housing 110 that opens at a lower outlet through hole 128a in a lateral channel 132 on the lower or bottom surface of the Ussing chamber assembly 100.

Figure 3:
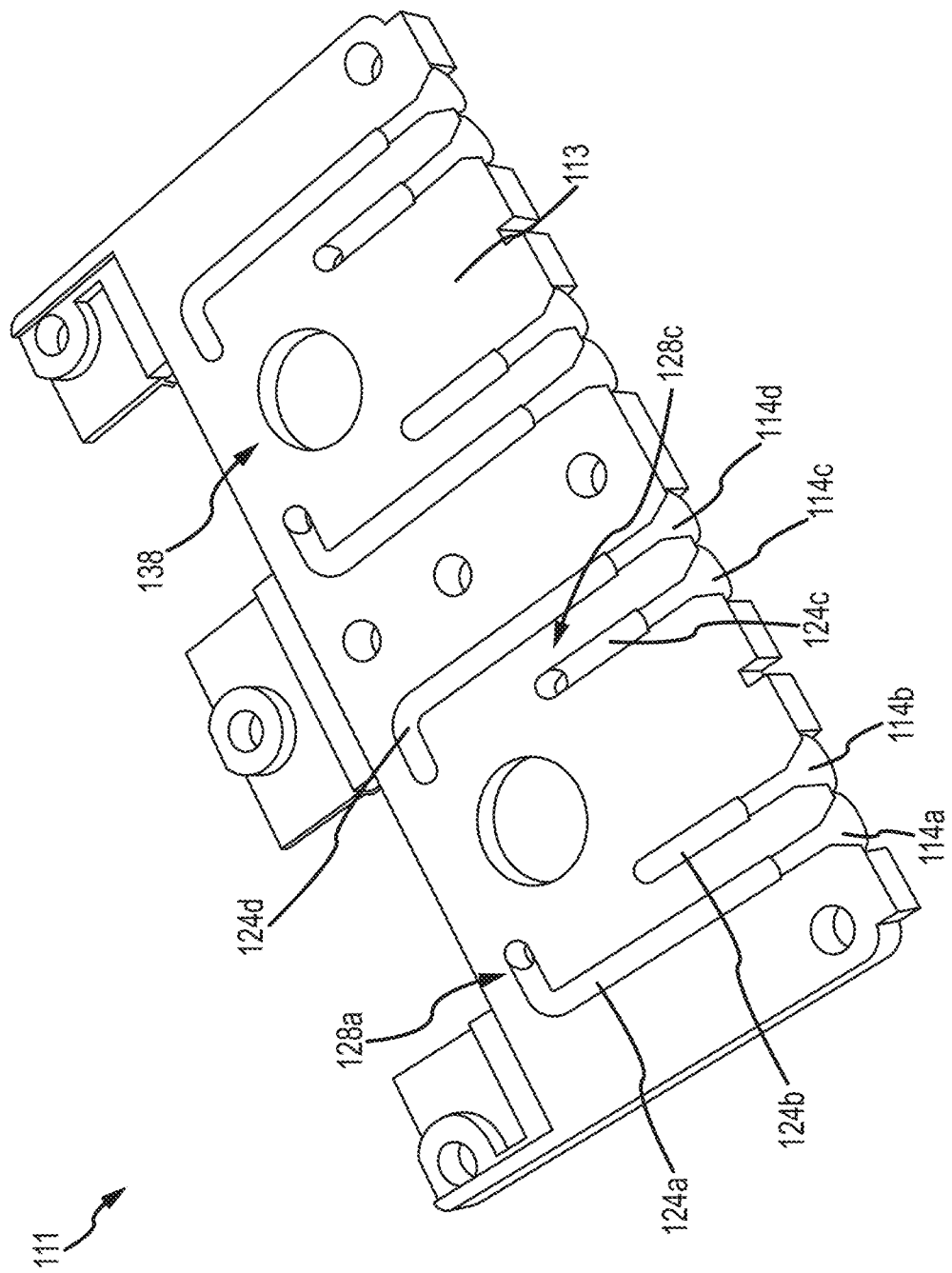
FIG. 3 is a bottom, rear, left-side perspective view of a housing half from the partially assembled Ussing chamber of FIG. 1.

As shown in FIG. 3, the housing half 111 defines a lower inlet channel 124a between the lower inlet port 114a and the lower outlet through hole 128a. Returning to FIG. 2, the lateral channel 132 is partially defined by a lateral channel wall 133. In addition to the lower outlet through hole 128a, the lateral channel wall 133 circumscribes an insert landing 136, an insert through hole 138, and a lower inlet through hole 128c. The lower inlet through hole 128c is located across the lateral channel 132 from the lower outlet through hole 128a with the insert landing 136 and insert through hole 138 located therebetween. The lower inlet through hole 128c is the starting point of another fluid pathway that opens on the front face of the housing 110 at a lower outlet port 114c.

Returning to FIG. 3, the housing half 111 defines a lower outlet channel 124c between the lower inlet through hole 128c and the lower outlet port 114c. The nomenclature of "inlet" and "outlet" with regard to the lower inlet port 114a, lower outlet port 114c, lower inlet channel 124a, lower outlet channel 124c, lower outlet through hole 128a, and the lower inlet through hole 128c is arbitrary named as the direction of flow along this pathway is determined by which port a fluid pump or pressure source is connected. The same applies to an upper flow pathway which will be described next.

Returning to FIG. 2, an upper inlet port 114d is the starting point of a fluid pathway through the housing 110 that opens at an upper outlet through hole 128d (FIG. 1) in the lateral channel 132 on the upper or top surface of the Ussing chamber assembly 100. As shown in FIG. 3, the housing half 111 defines an upper inlet channel 124d between the upper inlet port 114d and the upper outlet through hole 128d. As shown in FIG. 1, an upper inlet through hole 128b is located across the lateral channel 132 from the lower outlet through hole 128d. The upper inlet through hole 128b is the starting point of another fluid pathway that opens on the front face of the housing 110 at an upper outlet port 114b. Returning to FIG. 3, the housing half 111 defines an upper outlet channel 124b between the upper inlet through hole 128b and the upper outlet port 114b.

As discussed above, the lateral channel 132 (FIGS. 1 and 2) may be partially defined by the lateral channel wall 133, it may also be partially defined by a lateral channel sealing gasket (not shown) configured to be positioned in a gasket landing 130. The lateral channel sealing gasket provides a vertical sealing surface between lateral channel wall 133 and the glass cover 160 (which is discussed in more detail below). The gasket landing 130 provides a seating surface for the lateral channel sealing gasket to help keep it positioned properly.

Figure 5:
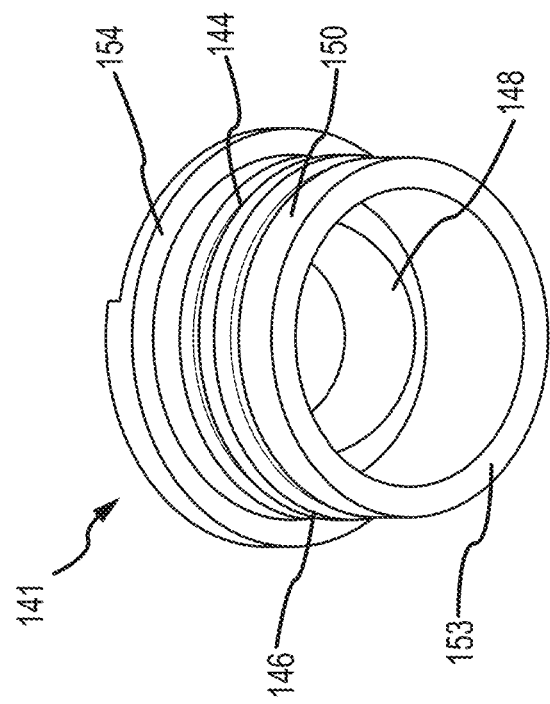
FIG. 5 is a bottom, rear perspective view of the upper insert from FIG. 4.
Figure 4:
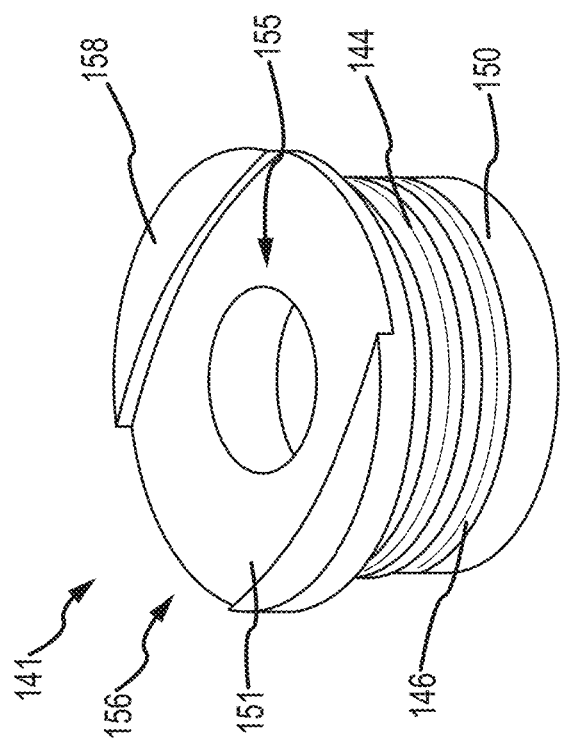
FIG. 4 is a top, front perspective view of an upper insert from the partially assembled Ussing chamber of FIG. 1.
Figure 7:
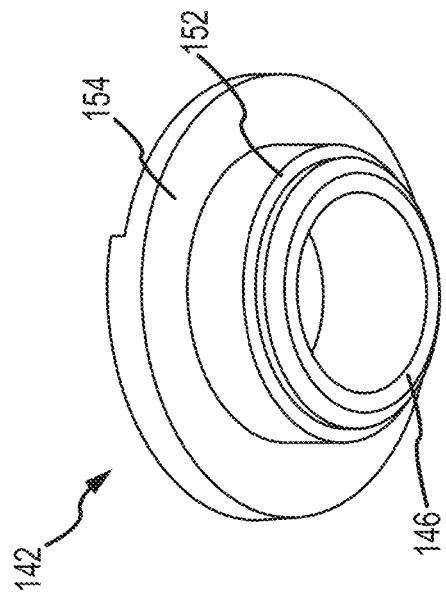
FIG. 7 is a bottom, rear perspective view of the lower insert from FIG. 6.
Figure 6:
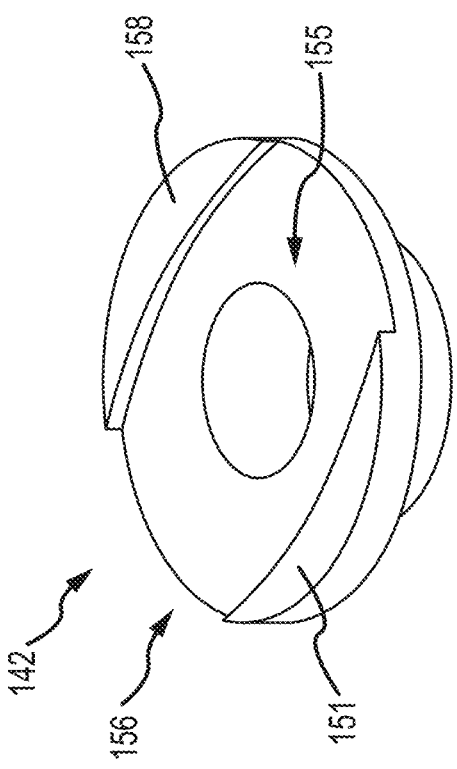
FIG. 6 is a top, front perspective view of a lower insert from the partially assembled Ussing chamber of FIG. 1.

As shown in FIGS. 8 and 9, the insert subassembly 140 may be comprised of an upper insert 141 (shown in FIGS. 4 and 5) and a lower insert 142 (shown in FIGS. 6 and 7). As with the housing halves 111, the upper and lower inserts 141, 142 may be comprised of a polymeric material, such as PTFE or COC. As shown in FIGS. 4 and 5, the upper insert 141 may have an upper cylindrical wall 150 and a cylindrical head 151 connected to the top of the cylindrical wall 150. The cylindrical head 151 may have a pair of insert arms 158 extending vertically above it and defining an insert channel 156 therebetween. The cylindrical head 151 may have an annular abutment surface 154 on a downwardly facing surface thereof.

FIG. 1 shows the upper insert 141 positioned within an insert through hole 138. The annular abutment surface 154 of the insert 141 is configured to abut the insert landing 136 on housing half 111. When the upper insert 141 is positioned within the insert through hole 138, the upper insert 141 may be rotatable about a longitudinal axis thereof such that inwardly facing vertical surfaces of the insert arms 158 align with inwardly facing vertical surfaces of the lateral channel wall 133 to become flush with one another.

Turning to FIGS. 6 and 7, the lower insert 142 may have a lower cylindrical wall 152 and a cylindrical head 151. The lower cylindrical wall 152 may have an outer diameter slightly less than an inner diameter of the upper cylindrical wall 150 of the upper insert 141 (see FIG. 9). As with the upper insert 141, the cylindrical head 151 of the lower insert 141 may have a pair of insert arms 158 extending vertically above it and defining an insert channel 156 therebetween. The cylindrical head 151 may have an annular abutment surface 154 on a downwardly facing surface thereof. FIG. 2 shows the lower insert 142 positioned within the insert through hole 138. The annular abutment surface 154 of the insert 141 is configured to abut the insert landing 136 on housing half 111. When the lower insert 142 is positioned within the insert through hole 138, the lower insert 142 may be rotatable about a longitudinal axis thereof such that inwardly facing vertical surfaces of the insert arms 158 align with inwardly facing vertical surfaces of the lateral channel wall 133 to become flush with one another.

FIG. 9 shows the lower cylindrical wall 152 of the lower insert 142 positioned radially inside the upper cylindrical wall 150 of the upper insert 141. Each of the upper and lower inserts 141, 142 may have an annular tissue landing surface 148 located radially inward from the upper and lower cylindrical walls 150, 152, respectively, and having identical diameters to each other. The annular tissue landing surface 148 may be adjacent a radially inwardly facing cylindrical surface defining an insert through hole 155 coaxial with the insert through hole 138. The annular tissue landing surfaces 148 of the upper and lower inserts 141, 142 are configured to hold the tissue sample axially therebetween. Further, the annular tissue landing surfaces 148 may be adjacent a radially outwardly facing tissue gripping barb 149 which is configured to grip and retain the tissue sample along a circumferential edge thereof. The upper insert 141 may have a bottom stop surface 153 which is the bottom-most surface of the cylindrical wall 150. The bottom stop surface 153 may be configured to abut the annular abutment surface 154 of the lower insert 142 to define a minimum spacing between the annular tissue landing surfaces 148.

As shown in FIGS. 1 and 2, when the bottom stop surface 153 engages the annular abutment surface 154 of the lower insert 142 and the insert subassembly 140 is positioned inside the insert through hole 138, the top surface of the insert arms 158 may be flush with the top surface of the lateral channel wall 133 and the top surface of the insert channel 156 may be flush with top surface of the lateral channel 132. In addition, as shown in FIGS. 4 and 5, the outer surface of the upper cylindrical wall 150 may have an upper groove 144 and a lower groove 146 each configured to seat an O-ring or gasket (not shown). When the upper insert 141 is positioned in the insert through hole 138, the O-rings or gaskets in the upper and lower grooves 144, 146 may be configured to engage an inwardly facing surface of a respective housing half 111 to form a lower seal for helping to ensure that fluid in the lateral channel 132 and insert channel 156 on each side of the housing 110 do not cross-contaminate each other.

The Ussing chamber assembly 100 may include a plurality of insert subassemblies 140 having different upper and lower cylindrical wall (150, 152) heights and/or different annular tissue landing surface (148) axial positions resulting in different minimum spacing distances between the annular tissue landing surfaces 148 to accommodate different thicknesses of tissue samples. For example, the Ussing chamber assembly 100 may be configured to have a first insert subassembly 140 in a first Ussing chamber 101a and a second insert subassembly 140 in a second Ussing chamber 101b wherein the first and second insert subassemblies 140 are configured to hold tissue samples 442 having different thicknesses so as to simultaneously test different thicknesses of the same type of tissue sample.

It may be desired for the annular tissue landing surfaces 148 to hold the tissue sample in compression. Thus, the thickness of the tissue sample may be selected to be larger than the minimum spacing between the annular tissue landing surfaces 148. By doing so, the top surfaces of one or both sets of the insert arms 158 may sit higher than the top surface of the lateral channel walls 133 when the annular tissue landing surfaces 148 contact without compressing the tissue sample. Accordingly, as shown in FIGS. 10 and 11, the upper and lower clamps 104, 106 may apply a compressive force directly to the glass covers 160 which is transmitted through the lateral channel sealing gaskets in parallel with the insert subassembly 140 to compress the tissue sample. In other words, the glass cover 160 is configured to directly contact both the lateral channel sealing gasket and the insert subassembly 140 before compressing the tissue sample 102. Compressing the lateral channel sealing gasket may help fix the radial positions of the upper and lower inserts 141, 142 to maintain alignment of the insert channels 156 with the lateral channels 132.

Returning to FIGS. 1 and 2, the outer side surfaces 112 of the housing halves 111 may have a rectangular wall 117 extending upward. The rectangular wall 117 may be dimensioned to be larger than the glass cover 160, thus, providing a glass cover well 118 for the glass cover 160 to sit or actuate vertically inside. In some embodiments, the top surface of the rectangular wall 117 may be the outer side surface 112 (rather than having a thin wall as shown), and the glass cover well 118 may simply be a recess within the outer side surface 112. The height of the rectangular wall 117 may be larger than the thickness of the glass cover 160 but less than the combined thickness of the glass cover 160 and the thickness of the lateral channel sealing gasket. Various materials and thicknesses of the lateral channel sealing gasket may be chosen to provide a desired amount of compression of the tissue sample when the upper and lower clamps 104, 106 are fully clamped onto the housing 110 and glass cover 160. The Ussing chamber 101a, 101b may be considered the volume including the upper and lower glass covers 160 and the projection of the glass covers 160 between them. The Ussing chambers 101a, 101b may be separated into a first portion of the chamber and a second portion of the chamber when a tissue is loaded between the annular tissue landing surfaces 148 (i.e., for when the Ussing chamber is divided into two volumes no longer in fluid communication with each other). As an example, the size of Ussing chambers 101a, 101b may be less than 5 cm×5 cm×3 cm, less than 4 cm×4 cm×3 cm, less than 3 cm×3 cm×2 cm, and preferably equal or less than 2.5 cm×2.5 cm×1 cm.

Turning to FIG. 10, the upper clamp 104 may have an upper window 105 for each Ussing chamber 101a, 101b to permit visual inspection of and through the glass cover 160 and microscopy of the tissue sample 102. The window 105 may have an opening smaller than the size of the glass cover 160 or at least one or more edges offset from the edges of the glass cover 160 to ensure that the upper clamp 104 engages a portion of the glass cover 160. The lower clamp 106 may also have a lower window 107 for each Ussing chamber 101a, 101b to permit visual inspection of and through the glass cover 160 and microscopy of the tissue sample 102. The lower windows 107 may be the same size and shape as the upper windows 105 or, as shown in FIG. 11, the lower window 107 may have a circular opening slightly larger than the insert through hole 155. Each of the upper and lower clamps 104, 106 and the housing 110 may have a plurality of fastener through holes 122 surrounding each Ussing chamber 101a, 101b to permit a fastener such as a screw to pass through for engaging a nut or any other fastening system known to those having ordinary skill in the art. The upper and lower clamps 104, 106 may be comprised of the same material or a harder material than the housing 110 to help evenly distribute clamping forces on the glass cover 160 and/or the housing 110. Microscopy may be performed separately on the Ussing chamber 101a, 101b through the upper and lower windows 105, 107 during testing, which includes while fluid is flowing through any of the channels 124a-124d or through the lateral channel 132 as discussed above. Moreover, the Ussing chambers 101a, 101b may be oriented in any orientation with respect to gravity as a reference vertical direction. In particular, the Ussing chambers 101a, 101b may be rotated at any angle, such as 45, 90, or 180 degrees in any of three different orthogonal directions during testing, which includes while fluid is flowing through any of the channels 124a-124d or through the lateral channel 132.

Figure 12:
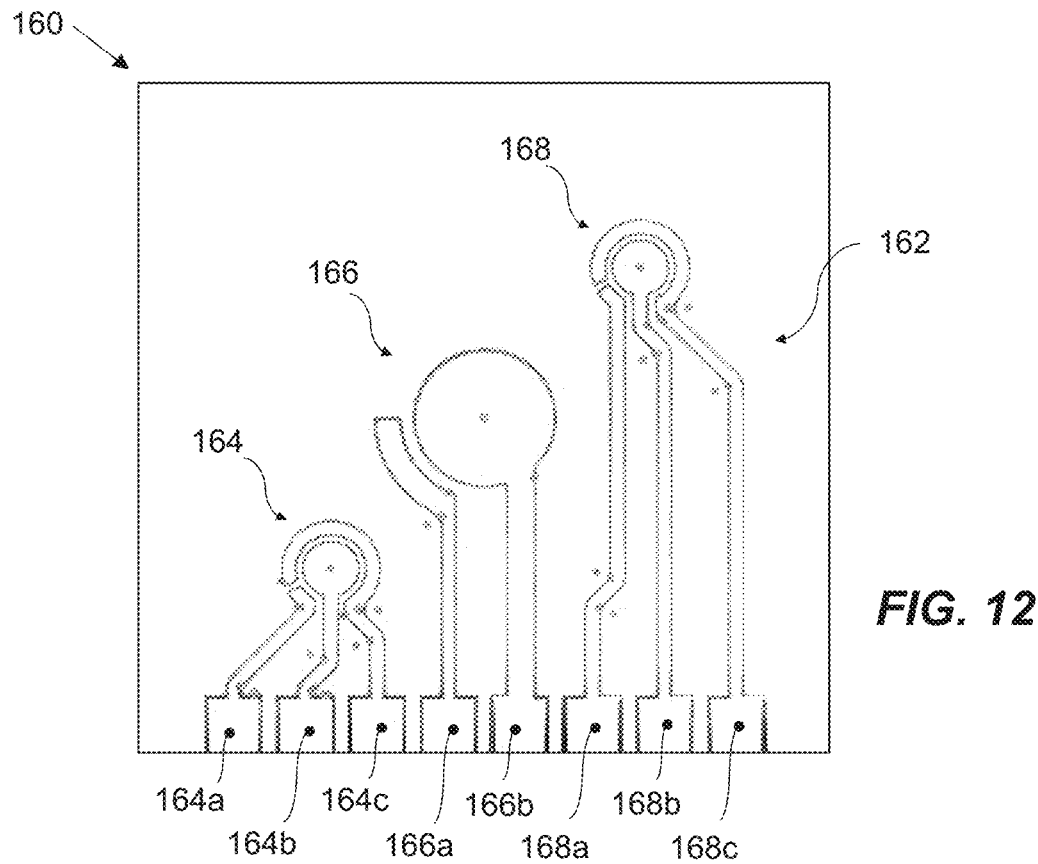
FIG. 12 is a top view of an electrode layout of a glass cover from the partially assembled Ussing chamber of FIG. 1.

FIG. 12 shows a top view of the glass cover 160 showing the electrodes 162. The electrodes 162 may be located on the inwardly facing surface of the glass cover 160 and positioned within the perimeter of the lateral channel sealing gasket so that the electrodes 162 are configured to contact the fluid as it flows across the lateral channel 132. The electrodes 162 may be grouped into electrode groups, such as: near electrodes 164 having a near counter electrode 164a, a near working electrode 164b, and a near reference electrode 164c; central electrodes 166 having a center working electrode 166a and a center reference electrode 166b; and far electrodes 168 having a far counter electrode 168a, a far working electrode 168b, and a far reference electrode 168c. The center electrodes 162 may be configured to measure Trans-Epithelial Electrical Resistance (TEER) and/or pH. The center reference electrode 166b may comprise indium tin oxide (ITO) and the center working electrode 166a may comprise gold. The near and far electrodes 164, 168 may be configured to measure oxygen, glucose, lactose, or any other electrochemical sensor with or without surface modifications. The near and far counter and working electrodes 164a, 164b, 168a, 168b may be comprised of gold and the near and far reference electrodes 164c, 168c may be comprised of silver/silver chloride and may be modified by Nafion, glucose oxidase enzyme (GOx), lactose oxidase enzyme (LOx), etc.

The electrodes 162 may have electrical contacts along a same edge of the glass cover 160. As shown in FIG. 10, the upper and lower clamps 104, 106 may be configured to lower the glass cover 160 downward toward an electrode connector 172 on the breakout board 170 such that each of the electrodes 160 makes electrical contact with a connector pin 174. The connector pins 174 may be spring loaded to handle various vertical positions of the glass cover 160 with respect to the breakout board 170.

Figure 13:
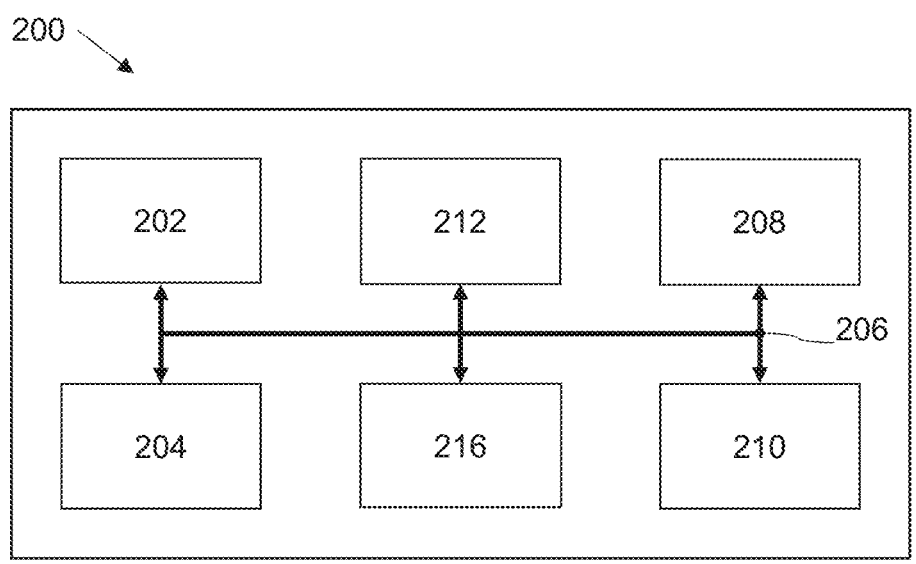
FIG. 13 is a block diagram of a computing and networking environment 200.

FIG. 13 illustrates an example of a suitable computing and networking environment 200 that may be used to implement various aspects of the present disclosure described in FIG. 13, among others. As illustrated, the computing and networking environment 200 includes a general purpose computing device 200 capable of operating the functions of the Ussing chamber assembly 100 of FIGS. 10 and 11, although it is contemplated that the networking environment 200 may include other computing systems, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the computer 200 may include various hardware components, such as a processing unit 202, a data storage 204 (e.g., a system memory), and a system bus 206 that couples various system components of the computer 200 to the processing unit 202. The system bus 206 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 200 may further include a variety of computer-readable media 208 that includes removable/non-removable media and volatile/nonvolatile media, but excludes transitory propagated signals. Computer-readable media 208 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computer 200. Communication media includes computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The data storage or system memory 204 includes computer storage media in the form of volatile/nonvolatile memory such as read only memory (ROM) and random access memory (RAM). A basic input/output system (BIOS), containing the basic routines that help to transfer information between elements within the computer 200 (e.g., during start-up) is typically stored in ROM. RAM typically contains data and/or program modules that are immediately accessible to and/or presently being operated on by processing unit 202. For example, in one embodiment, data storage 204 holds an operating system, application programs, and other program modules and program data.

Data storage 204 may also include other removable/non-removable, volatile/nonvolatile computer storage media. For example, data storage 204 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media, described above and illustrated in FIG. 13, provide storage of computer-readable instructions, data structures, program modules and other data for the computer 200.

Figure 15:
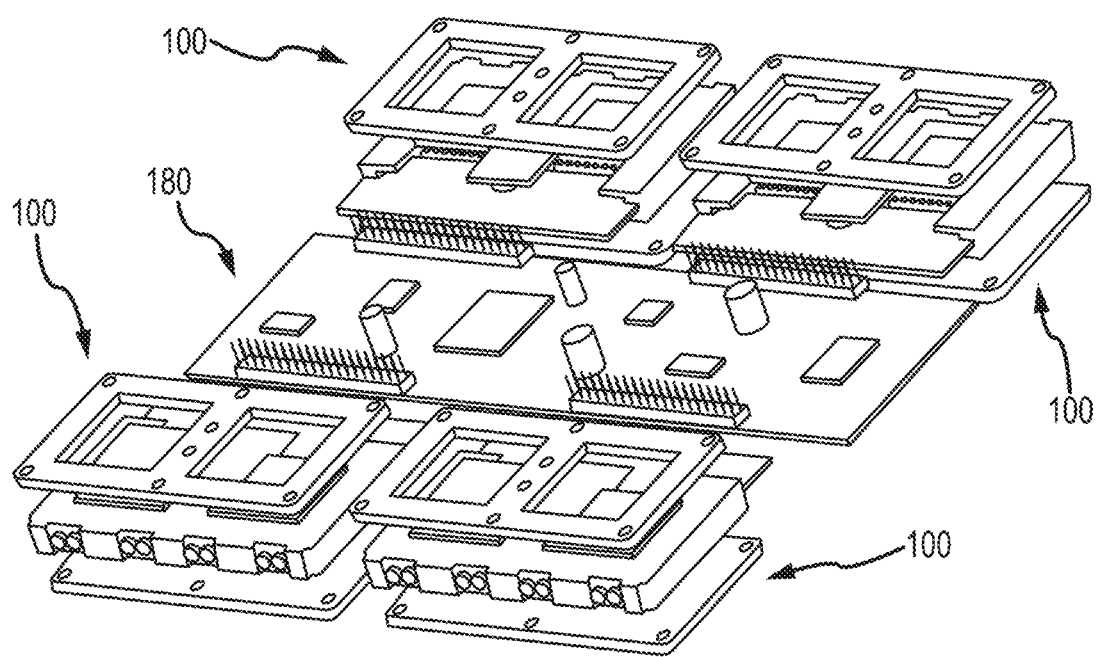
FIG. 15 is a top, rear, left-side perspective view of a multiple Ussing chamber device.

A user may enter commands and information through a user interface 210 or other input devices such as a tablet, electronic digitizer, a microphone, keyboard, and/or pointing device, commonly referred to as mouse, trackball or touch pad. Other input devices may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices are often connected to the processing unit 202 through a user interface 210 that is coupled to the system bus 206, but may be connected by other interface and bus structures, such as a parallel port, game port or a universal serial bus (USB). A monitor 212 or other type of display device is also connected to the system bus 206 via an interface, such as a video interface. The monitor 212 may also be integrated with a touch-screen panel or the like. FIG. 15 shows an exemplary graphical user interface 214 that may be shown on the monitor 212.

Referring back to FIG. 13, the computer 200 may operate in a networked or cloud-computing environment using logical connections of a network interface or adapter 216 to one or more remote devices, such as a remote computer. The remote computer may be a personal computer, a server, a router, a network PC, a peer device or other common network node, and typically includes many or all of the elements described above relative to the computer 200. The logical connections depicted in FIG. 13 include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computer 200 may be connected to a public and/or private network through the network interface or adapter 216. In such embodiments, a modem or other means for establishing communications over the network is connected to the system bus 206 via the network interface or adapter 216 or other appropriate mechanism. A wireless networking component including an interface and antenna may be coupled through a suitable device such as an access point or peer computer to a network. In a networked environment, program modules depicted relative to the computer 200, or portions thereof, may be stored in the remote memory storage device.

Figure 14:
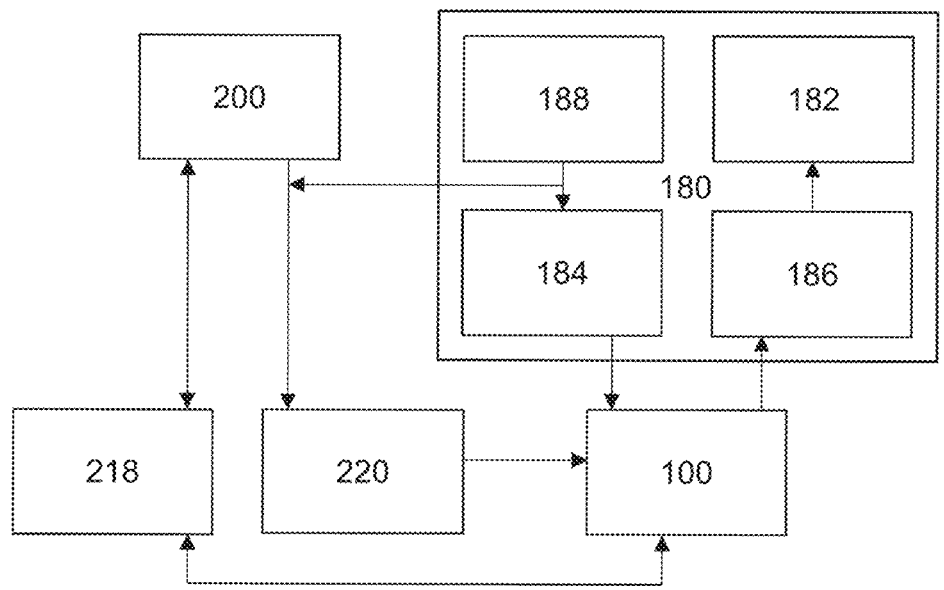
FIG. 14 is a block diagram of an Ussing chamber system.
Figure 16:
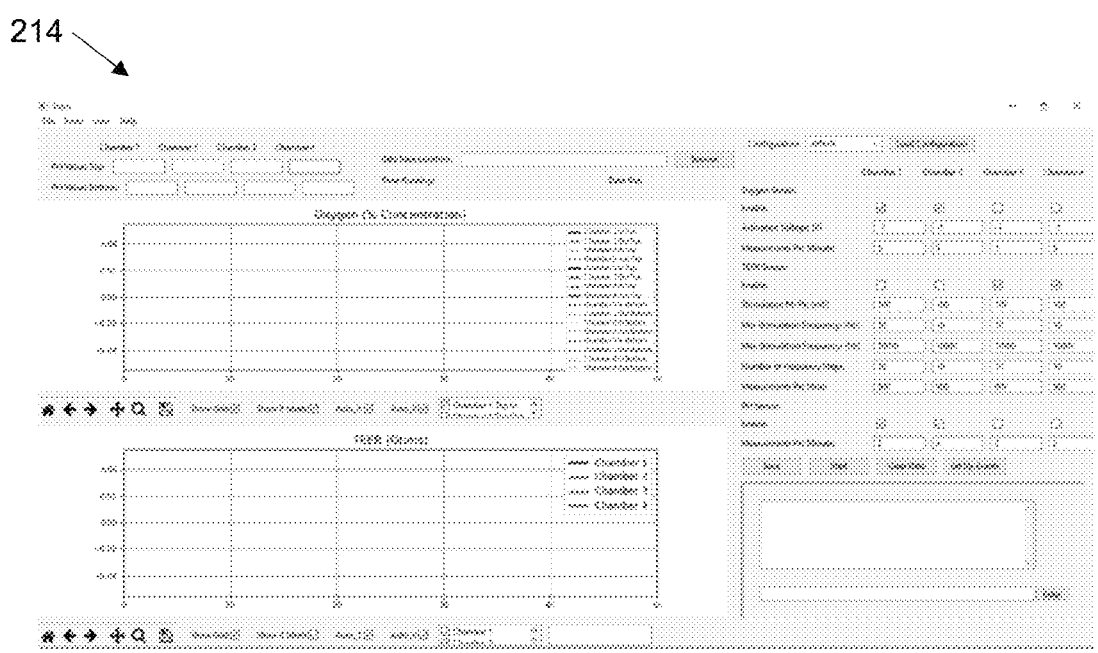
FIG. 16 is a graphical user interface from the monitor shown in FIG. 13.

FIG. 14 shows a block diagram of Ussing chamber system. In the system, a user may interact with the computer 200 discussed above. In one example, a user may interact with the graphics user interface 214 as shown in FIG. 16 to configure and measure various parameters of the Ussing chamber assembly 100. For example, a user may configure or interact with a microfluidic system to provide precise amounts of various fluids to the Ussing chamber assembly 100. An external pump 220, such as a syringe pump, may be in fluidic communication with the inlet and outlet ports 114a-114d to deliver a liquid substance from a fluid reservoir to the tissue sample 102, such as a buffer solution, a drug, or any other substance to interact with the tissue sample 102. In addition, two or more external pumps 220 may be used to deliver multiple liquid substances. The computer 200 may initiate various commands to the external pump 220 to control the delivery of the liquid substance.

The block diagram in FIG. 14 also shows the computer 200 interacting with a circuit board 180, which is also shown in FIG. 15. The circuit board 180 may be configured to connect to a plurality of Ussing chamber assemblies 100, such as 1, 2, 3, or 4. In other embodiments not shown, the circuit board 180 may connect to any number of Ussing chamber assemblies 100 such as 6, 8, 10, 12, 16, 24, 32, 48, 64, or 96 Ussing chamber assemblies 100. Returning to FIG. 14, the circuit board 180 may include an ND converter 182, a microcontroller 188, a stimulus generation unit 184, and a sensor read channel unit 186, among other electronics devices and circuitry elements. The aforementioned units on the circuit board 180 may include potentiometry and/or amperometry circuitry.

In addition, an external optical microscope 218 may be optically connected to the Ussing chamber assembly 100 to capture images and/or record video during data acquisition therefrom. As shown in FIG. 14, the computer 200 may initiate various commands to the external optical microscope 218 and may acquire and save images generated therefrom. The computer 200 may also be connected to an incubator or temperature controller (not shown) for controlling the temperature of the Ussing chamber assembly 100.

It should be understood from the foregoing that, while particular aspects have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An Ussing chamber assembly for assessing a tissue sample and for receiving a first fluid and a second fluid during such assessment, the Ussing chamber assembly comprising:
   an insertable Ussing chamber having an insert to retain the tissue sample positioned therein to isolate the Ussing chamber into a first chamber portion and a second chamber portion, the insert comprising an annular tissue landing surface located configured to hold the tissue sample so that a first side of the tissue sample is located within the first chamber portion and a second side of the tissue sample is located within the second chamber portion;
   a housing configured to receive the insertable Ussing chamber,
   the housing defining a first fluidic channel configured, at least, to route the first fluid to the first chamber portion and a second fluidic channel configured to, at least, route the second fluid to the second chamber portion;
   a glass cover positioned above the tissue sample in the first chamber portion, the glass cover comprising at least three integrated electrical sensors in contact with the first fluid; and
   a measurement circuitry configured to measure, via the at least three integrated electrical sensors, a plurality of measurements relating to the tissue sample simultaneously.

2. The Ussing chamber assembly of claim 1, wherein the measurement circuitry is configured to measure a Trans-Epithelial Electrical Resistance and at least one of pH, oxygen level, glucose level, and lactose level in the first chamber portion.

3. The Us sing chamber assembly of claim 2, wherein the measurement circuitry is configured to measure at least one of pH, oxygen level, glucose level, and lactose level in the second chamber portion.

4. The Us sing chamber assembly of claim 2, wherein the measurement circuitry is configured to measure at least two of pH, oxygen level, glucose level, and lactose level in the first chamber portion.

5. The Us sing chamber assembly of claim 4, wherein the measurement circuitry is configured to measure at least three of pH, oxygen level, glucose level, and lactose level in the first chamber portion.

6. The Ussing chamber assembly of claim 1, wherein microscopy is configured to be performed separately on both the first chamber portion and the second chamber portion while the first fluid is flowing through the first fluidic channel and the second fluid is flowing through the second fluidic channel.

7. The Ussing chamber assembly of claim 6, wherein the Ussing chamber is configured to be rotated 90 degrees in any of three different orthogonal directions during a measurement and while the first fluid is flowing in the first fluidic channel and while the second fluid is flowing in the second fluidic channel.

8. The Ussing chamber assembly of claim 1, further comprising: a second glass cover positioned under the tissue sample in the second chamber portion, the second glass cover comprising at least another three integrated electrical sensors in contact with the second fluid.

9. A measurement device configured for measuring one or more properties of two separate sides of a tissue sample and for receiving a first fluid and second fluid during such measurement, the measurement device comprising:
   an insertable Ussing chamber having an insert to retain the tissue sample into a first chamber portion and a second chamber portion, the insdert comprising an annular tissue landing surface configured to hold the tissue sample so that a first side of the tissue sample is located within the first chamber portion and a second side of the tissue sample is located within the second chamber portion;
   a housing configured to receive the insertable Ussing chamber,
   the housing defining a first fluidic channel configured, at least, to route the first fluid to the first chamber portion and a second fluidic channel configured to, at least, route the second fluid to the second chamber portion;
   a glass cover positioned above the tissue sample in the first chamber portion, the glass cover comprising at least three integrated electrical sensors in contact with the first fluid; and
   a measurement circuit configured to measure, via the at least three integrated electrical sensors, a plurality of measurements relating to the tissue sample simultaneously,
   wherein the housing is configured to be rotated 90 degrees in any of three different orthogonal directions during a measurement and while the first fluid is flowing in the first fluidic channel and while the second fluid is flowing in the second fluidic channel.

10. The measurement device of claim 9, wherein microscopy is configured to be performed separately on both the first and second chamber portions while the first fluid is flowing through the first fluidic channel and the second fluid is flowing through the second fluidic channel.

11. The measurement device of claim 9, wherein the measurement circuit is configured to measure a Trans-Epithelial Electrical Resistance and at least one of pH, oxygen level, glucose level, and lactose level in the first chamber portion.

12. The measurement device of claim 11, wherein the measurement circuit is configured to measure at least two of pH, oxygen level, glucose level, and lactose level in the first chamber portion.

13. The measurement device of claim 11, wherein the measurement circuit is configured to measure at least three of pH, oxygen level, glucose level, and lactose level in the first chamber portion.

14. The measurement device of claim 13, wherein the measurement circuit is configured to measure at least one of pH, oxygen level, glucose level, and lactose level in the second chamber portion.

15. The measurement device of claim 9, wherein a largest dimension of the housing in a first direction is less than 5 cm.

16. A measurement device configured for measuring one or more properties of a tissue sample and receiving a first fluid from a first removable fluid source and a second fluid from a second removable fluid source during such measurement, the measurement device comprising:
   an insertable Ussing chamber having an insert to retain the tissue sample into a first chamber portion and a second chamber portion, the insert comprising an annular tissue landing surface configured to hold the tissue sample so that a first side of the tissue sample is located within the first chamber portion and a second side of the tissue sample is located within the second chamber portion;
   a housing configured to receive the insertable Ussing chamber,
   the housing defining a first fluidic channel configured, at least, to route the first fluid to the first chamber portion and a second fluidic channel configured to, at least, route the second fluid to the second chamber portion;
   the first chamber portion having a first integrated fluid port configured to be connected to the first removable fluid source;
   the second chamber portion having a second integrated fluid port configured to be connected to the second removable fluid source;
   a glass cover positioned above the tissue sample in the first chamber portion, the glass cover comprising at least three integrated electrical sensors in contact with the first fluid; and
   a measurement circuit configured to measure, via the at least three integrated electrical sensors, a plurality of measurements relating to the tissue sample simultaneously,
   wherein a largest dimension of the Us sing chamber in a first direction is less than 5 cm.

17. The measurement device of claim 16, wherein a largest dimension of the Us sing chamber in the first direction and in a second direction is less than 4 cm.

18. The measurement device of claim 17, wherein a largest dimension of the Ussing chamber in a third direction orthogonal to the first and second directions is less than 3 cm.

19. The measurement device of claim 17, wherein microscopy is configured to be performed separately on both the first and second chamber portions while the first fluid is flowing through the first fluidic channel and the second fluid is flowing through the second fluidic channel.

20. The measurement device of claim 17, wherein the Us sing chamber is configured to be rotated 90 degrees in three different orthogonal directions during a measurement and while the first fluid is flowing in the first fluidic channel and while the second fluid is flowing in the second fluidic channel.

* * * * *